US00PP25657P3

(12) United States Plant Patent
Layt

(10) Patent No.: US PP25,657 P3
(45) Date of Patent: Jun. 30, 2015

(54) *HARDENBERGIA VIOLACEA* PLANT NAMED 'HB1.08'

(50) Latin Name: *Hardenbergia violacea*
Varietal Denomination: HB1.08

(71) Applicant: Todd Layt, Richmond (AU)

(72) Inventor: Todd Layt, Richmond (AU)

( * ) Notice: Subject to any disclaimer, the term of this patent is extended or adjusted under 35 U.S.C. 154(b) by 294 days.

(21) Appl. No.: 13/694,562

(22) Filed: Dec. 12, 2012

(65) Prior Publication Data

US 2014/0165244 P1 Jun. 12, 2014

(51) Int. Cl.
*A01H 5/00* (2006.01)

(52) U.S. Cl.
USPC ..... Plt./226
CPC ..... *A01H 5/00* (2013.01)

(58) Field of Classification Search
USPC ..... Plt./226, 263.1
CPC ..... A01H 5/00; A01H 5/02
See application file for complete search history.

*Primary Examiner* — Kent L Bell
(74) *Attorney, Agent, or Firm* — Samuel R. McCoy, Jr.

(57) ABSTRACT

'HB1.08' is a distinctive variety of *Hardenbergia violacea* which is characterized by long and narrow foliage, short petioles, reduced internode length, and a great number of inflorescences.

2 Drawing Sheets

Latin name of the genus and species: The Latin name of the genus and species of the novel variety disclosed herein is *Hardenbergia violacea.*

Variety denomination: The inventive variety of *Hardenbergia violacea* disclosed herein has been given the variety denomination 'HB1.08'.

BACKGROUND OF THE INVENTION

*Hardenbergia violacea* is a flowering vine or subshrub native to Australia which belongs to the pea family, Fabaceae. Flowers are typical of the pea family and range in color from white to violet to pink. Foliage is usually dark green and leathery. *Hardenbergia* can be found in production throughout Australia and the United States. The present invention relates to a new and distinct perennial variety of *Hardenbergia violacea*, which has been given the variety denomination of 'HB1.08'. Its market class is that of an ornamental plant. 'HB1.08' is intended for use in landscaping and as a decorative plant.

Parentage: The *Hardenbergia violacea* variety 'HB1.08' was finally selected in 2010 in an Australian nursery in the state of New South Wales following a selection process carried out from 2008 to 2010 involving approximately 1000 seedlings of *Hardenbergia violacea* 'HB01' (unpatented) production stock. 'HB1.08' is a seedling selection from open pollinated *Hardenbergia violacea* 'HB01'. 'HB1.08' was selected due to its strong, woody stems and shortened internodes that give the instant variety a shrub habit as opposed to the subshrub habit of the parent. 'HB1.08' also displays a greater number of inflorescences when compared to 'HB01'.

Asexual Reproduction: 'HB1.08' was first propagated asexually by division in the state of New South Wales, Australia in 2010 and has since gone through 2 successive cycles of vegetative propagation. The distinctive characteristics of the inventive 'HB1.08' variety are stable from generation to generation; plants of the variety produced by asexual reproduction maintain the distinguishing characteristics of the original plant.

SUMMARY OF THE INVENTION

'HB1.08' is a distinctive variety of *Hardenbergia violacea* which is characterized by long and narrow foliage, short petioles, reduced internode length, and a great number of inflorescences.

BOTANICAL DESCRIPTION OF THE PLANT

Figure 1:
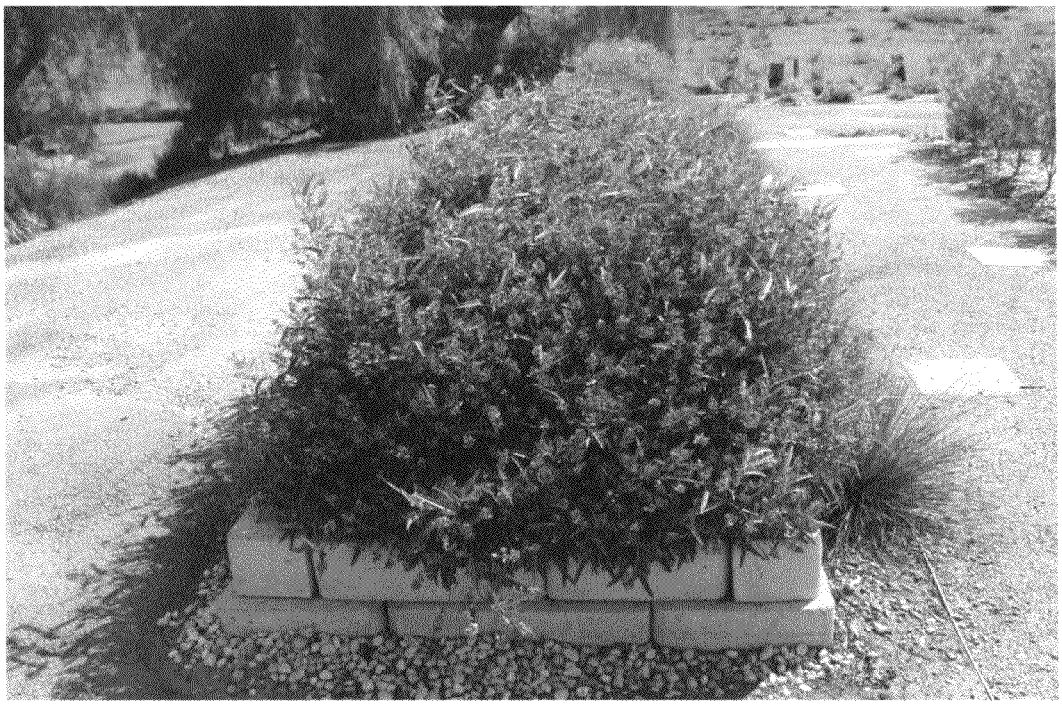
FIG. 1 illustrates a mature 'HB1.08' plant.
Figure 2:
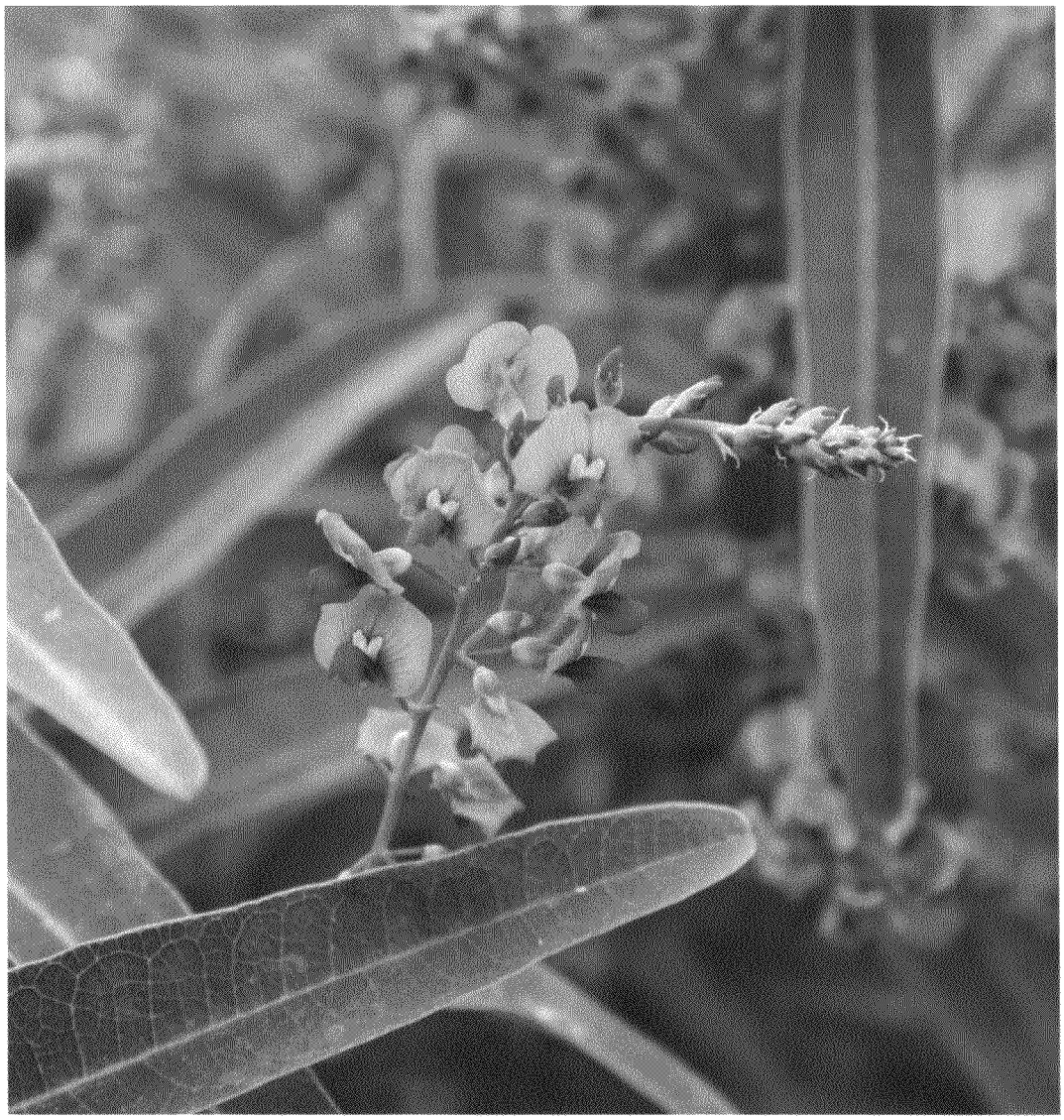
FIG. 2 illustrates the flower of a 'HB1.08' plant.

The following is a detailed botanical description of a new and distinct variety of a *Hardenbergia violacea* ornamental plant known as 'HB1.08'. Plant observations were made on plants grown in New South Wales, Australia. Unless indicated otherwise, the descriptions disclosed herein are based upon observations made from mature 'HB1.08' plants grown from rooted cuttings from November 2010 to September 2011 in 200 mm nursery pots filled with soilless potting media, maintained with granular slow release fertilizer and regularly watered with overhead irrigation. No pest and disease measures were taken. Plants were pruned lightly at approximately 4 months of age, when transplanted from 90 mm propagation pots into the 200 mm nursery pots.

Those skilled in the art will appreciate that certain characteristics will vary with older or, conversely, younger plants. 'HB1.08' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 1986 edition. Note that generic color descriptions such as 'white' do not exist in the R.H.S. charts and the corresponding R.H.S. colors are quoted.

'HB1.08' is a perennial *Hardenbergia violacea* plant which is a seedling selection from *Hardenbergia violacea* 'HB01' (unpatented). After its selection, 'HB1.08' was asexually propagated by division. 'HB1.08' has a shrub habit, deep violet flower color and long bloom period.

These features and other characteristics are apparent from the description provided below.

Growth Habit, Dimensions and Color

Plant description:

*Plant habit*.—Shrub habit, free of any twining; semi-upright and dense.

*Height*.—Measured at 50 cm (average).

*Width*.—Measured at 60 cm (average).

*Bloom period*.—Late winter through early spring.

*Hardiness*.—U.S.D.A. Zone 9 to 11.

*Environmental tolerances*.—Prefers full to filtered sun. Drought tolerant.

*Pest and disease susceptibility or resistance*.—In common with the species, none of note.

*Propagation*.—Propagation is accomplished using softwood cuttings. Roots well without rooting compound or hormone.

*Time to develop roots*.—2 to 4 weeks.

*Crop time*.—Approximately 8 months are needed to produce a 20-centimeter container with plant in flower, starting from a rooted cutting.

Stem:

*Branching and habit*.—Strong basal and axillary branching habit; branch attitude is semi-erect.

*Number of stems*.—Numerous; more than 30.

*Stem strength*.—Strong.

*Shape*.—Cylindrical.

*Stem color*.—Young stem is closest to green 143C.

*Stem dimensions*.—Mature stem is approximately 45 to 60 cm in length with a diameter of 4 to 6 mm near the base.

*Stem surface*.—Mature stems are woody, hard and smooth.

*Basal stem color*.—Ranges from greyed orange 177A to brown 200D.

*Internode length*.—35 to 40 mm.

*Tendrils*.—Absent.

Foliage:

*Type*.—Evergreen.

*Shape*.—Elliptical.

*Division*.—Simple.

*Apex*.—More obtuse than acute.

*Base*.—Rounded.

*Venation*.—Reticulated.

*Vein color* (*adaxial surfaces*).—144A.

*Vein color* (*abaxial surfaces*).—144B.

*Margins*.—Lightly undulated and entire.

*Arrangement*.—Alternate.

*Attachment*.—Petiolate.

*Texture*.—Leathery.

*Surfaces* (*adaxial surface*).—Glabrous.

*Surfaces* (*abaxial surface*).—Glabrous.

*Mature leaf dimensions*.—Average length 117.6 mm, average width 18.4 mm.

*Leaf color* (*adaxial surface*).—Juvenile: 144A; mature: closest to 137A.

*Leaf color* (*abaxial surface*).—Juvenile: 144A; mature: closest to 137C.

*Petiole*.—Short; 10 mm in length, average; width approximately 1 mm; color is yellow-green (RHS 144A).

*Stipules*.—Laminar and green (RHS 143C); glabrous; length is approximately 2 to 4 mm.

General flower description:

*Inflorescence*.—Numerous racemes arising from leaf axils and comprised of approximately 15 to 20 non-persistent florets. Attitude is semi-erect to horizontal. Length of racemes is approximately 10 to 12 cm with a width of approximately 4 cm.

*Peduncle dimensions*.—100 to 120 mm long and 2.5 mm wide, at the base.

*Peduncle color*.—Yellow-green (RHS 144A).

*Natural flowering season*.—In the northern hemisphere, mid-February through April.

*Floret*.—Corolla Dimensions — 11 mm across, at the widest point, with a depth of 10 mm from base of the calyx to the apex of the keel petals. Petal Arrangement — Typical pea type flower with standard, wing and keel petals. Standard Petal — Shape is rounded. Margins are entire. Approximately 11 mm across with a height of 8 mm. Color is purple violet 84C. Markings present near base of standard petal along midrib; color is yellow green 145C. Winged Petal — Shape is obovate; apex is broad and round; base is acute; margins are undulate. Approximately 6 mm long and 3 mm wide. Color of both surfaces is purple 82A. Keel Petal — Shape is falcate; apex is round; base is acute; margins are entire. Approximately 4 mm high and 2 mm wide. Color of both surfaces is purple 82A. Pedicel — Approximately 8 mm in length; width is approximately 1 mm. Color is red purple 58B. Calyx — Fused with five sepal lobes; total length of the calyx is 5 mm, as measured. Sepal lobes are deltoid in shape and measure 2.5 mm long from base to apex and 2.5 mm wide, at the base of the lobe. Apex is acute and margins are entire. Color of both surfaces is yellow-green 145D at the base of the calyx, transitioning to greyed purple 186C near the lobes. Fragrance — Non-fragrant.

*Bud*.—Naked; shape is that of an oblong sphere with a falcate profile; apex is rounded. Approximately 5 mm long and 3 mm wide. Colors are yellow green 145D close to the pedicel, transitioning to greyed purple 186C near the bud apex.

Fruit and seed production: Not yet observed.

Comparison of HB1.08 with Other Varieties of *Hardenbergia violacea*

'HB1.08' is similar in form and function to the parent 'HB1' in that both have a shrub habit; i.e. strong and woody stems, a semi upright habit and relatively dense foliage, whereas other cultivars known to the breeder have a twining subshrub or vine habit. Although 'HB1' and 'HB1.08' have a similar habit, 'HB1.08' is unique in that it has longer leaves and shortened internodes. The combination of these characteristics translates into a denser shrub with a greater number of flowers.

'HB1.08' has leaves that are, on average, 117.6 mm long and 18.4 mm wide (length-to-width ratio of 6.39) whereas the leaves of 'HB1' are 78.4 mm long and 18.3 mm wide (length-to-width ratio of 4.28). HB1.08 is a denser shrub due to the shortened internode length; the internodes of 'HB1.08' range from 35 to 40 mm long whereas the internodes of 'HB01' are from 50 to 60 mm long. Petiole length is yet another distinguishing factor that gives 'HB1.08' a more dense appearance when compared to 'HB1'. The petioles of 'HB1.08' are an average of 10 mm long whereas the petioles of 'HB1' are 14.5 mm on average. In both 'HB1' and 'HB1.08', flowering occurs at both primary and secondary leaf axils however because 'HB1.08' has more nodes and subsequently more axils per stem, more racemes are present. More racemes per stem ultimately translates into more flowers per plant.

The combination of its dense shrub habit and a greater number of flowers makes 'HB1.08' a desirable ornamental plant suited for mass production for pot and landscape use.

That which is claimed is:

1. A new and distinct variety of *Hardenbergia violacea* plant named 'HB1.08', substantially as described and illustrated herein.

* * * * *